(12) United States Patent  (10) Patent No.: US 8,671,544 B2
Xu et al.  (45) Date of Patent: Mar. 18, 2014

(54) METHODS AND MOULDS FOR USE IN FABRICATING SIDE-PORTED MICRONEEDLES

(75) Inventors: Yuan Xu, Singapore (SG); Minghua Wang, legal representative, Singapore (SG); Meí Ma Chen, Singapore (SG); Zhongli Li, Singapore (SG); Chee Yen Lim, Singapore (SG); Pei Ying Joyce Tan, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 1648 days.

(21) Appl. No.: 10/592,559

(22) PCT Filed: Mar. 12, 2004

(86) PCT No.: PCT/SG2004/000055
§ 371 (c)(1),
(2), (4) Date: Feb. 10, 2010

(87) PCT Pub. No.: WO2005/087305
PCT Pub. Date: Sep. 22, 2005

(65) Prior Publication Data
US 2010/0305516 A1  Dec. 2, 2010

(51) Int. Cl.
*B23P 25/00* (2006.01)
*B28B 1/48* (2006.01)
*B29C 33/00* (2006.01)
*B23P 17/00* (2006.01)

(52) U.S. Cl.
USPC ............. 29/458; 264/220; 264/154; 264/156; 29/527.1; 29/527.2; 29/527.3; 29/527.4; 29/527.5

(58) Field of Classification Search
USPC ................. 264/154, 156, 220, 225; 29/527.1, 29/527.2, 527.3, 527.4, 527.5, 458
See application file for complete search history.

(56) References Cited

U.S. PATENT DOCUMENTS

| | | | | |
|---|---|---|---|---|
| 4,838,877 A | * | 6/1989 | Massau | 604/272 |
| 5,573,519 A | * | 11/1996 | Zohmann | 604/272 |
| 5,848,996 A | * | 12/1998 | Eldor | 604/272 |
| 6,331,266 B1 | | 12/2001 | Powell et al. | |
| 6,334,856 B1 | | 1/2002 | Allen et al. | |
| 6,379,324 B1 | | 4/2002 | Gartstein et al. | |

(Continued)

FOREIGN PATENT DOCUMENTS

EP  1 088 642 B1  4/2001
EP  1 287 847 A1  5/2003

(Continued)

OTHER PUBLICATIONS

International Search Report under date of mailing of Jun. 9, 2004, and IPRP under date of Feb. 27, 2006 in connection with PCT/SG2004/000055.

*Primary Examiner* — Essama Omgba
(74) *Attorney, Agent, or Firm* — Quarles & Brady LLP

(57) ABSTRACT

A microneedle mold and a method of manufacturing a microneedle mold are provided for use in fabricating microneedles. The method includes providing a microneedle mold base with recesses therein, the recesses corresponding to the microneedles to be fabricated and extending from a first surface of the microneedle mold base; and forming side-port forming holes in the microneedle mold base, the side-port forming holes extend in side surfaces of the recesses within the microneedle mold base at side-port forming positions of the recesses.

33 Claims, 11 Drawing Sheets

(56) References Cited

U.S. PATENT DOCUMENTS

| | | |
|---|---|---|
| 6,440,096 B1 | 8/2002 | Lastovich et al. |
| 6,494,865 B1 | 12/2002 | Alchas |
| 6,503,231 B1 | 1/2003 | Prausnitz et al. |
| 6,533,949 B1 | 3/2003 | Yeshurun et al. |
| 6,558,361 B1 * | 5/2003 | Yeshurun ............... 604/272 |
| 6,569,143 B2 | 5/2003 | Alchas et al. |
| 6,589,202 B1 | 7/2003 | Powell |
| 6,611,707 B1 | 8/2003 | Prausnitz et al. |
| 6,749,792 B2 * | 6/2004 | Olson ................. 264/328.1 |
| 6,881,203 B2 * | 4/2005 | Delmore et al. ........ 604/272 |
| 6,899,838 B2 | 5/2005 | Lastovich |
| 7,578,954 B2 * | 8/2009 | Gartstein et al. ........ 264/154 |
| 7,666,172 B2 * | 2/2010 | Atil ....................... 604/272 |
| 7,981,346 B2 * | 7/2011 | Griss et al. ............. 264/299 |
| 2002/0020688 A1 * | 2/2002 | Sherman et al. ............ 216/2 |
| 2002/0053756 A1 | 5/2002 | Powell et al. |
| 2003/0009113 A1 * | 1/2003 | Olson ...................... 600/573 |
| 2003/0045837 A1 | 3/2003 | Delmore et al. |
| 2003/0135161 A1 | 7/2003 | Fleming et al. |
| 2003/0208138 A1 * | 11/2003 | Olson ...................... 600/573 |
| 2004/0164454 A1 * | 8/2004 | Gartstein et al. ......... 264/293 |
| 2005/0247666 A1 | 11/2005 | Lastovich |
| 2007/0255205 A1 * | 11/2007 | Griss et al. ............. 604/93.01 |
| 2009/0162798 A1 * | 6/2009 | Tomono ................... 430/320 |
| 2009/0326415 A1 * | 12/2009 | Lim ........................ 600/573 |
| 2012/0041337 A1 * | 2/2012 | Ferguson et al. ......... 600/573 |

FOREIGN PATENT DOCUMENTS

| | | | |
|---|---|---|---|
| WO | 9964580 A1 | 12/1999 | |
| WO | 0016833 A1 | 3/2000 | |
| WO | 0166065 A2 | 9/2001 | |
| WO | 03015860 A1 | 2/2003 | |
| WO | 03026732 A3 | 4/2003 | |
| WO | WO 2006025786 A1 * | 3/2006 | ............ A61M 37/00 |
| WO | WO 2008027011 A1 * | 3/2008 | ............ A61M 5/32 |

\* cited by examiner

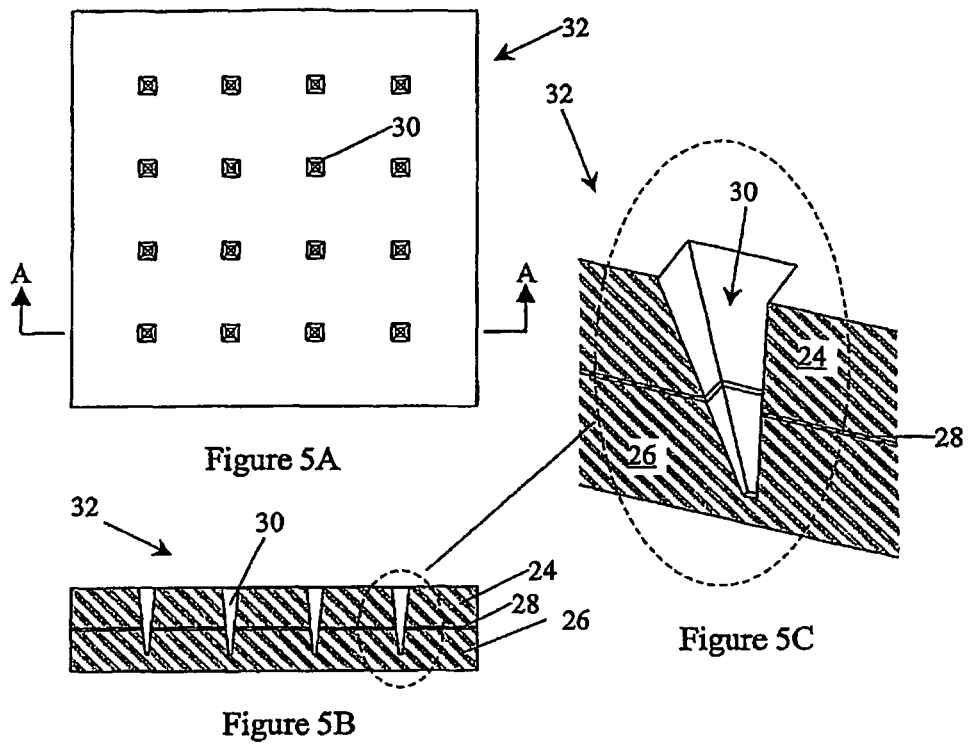
Figure 5A
Figure 5B
Figure 5C
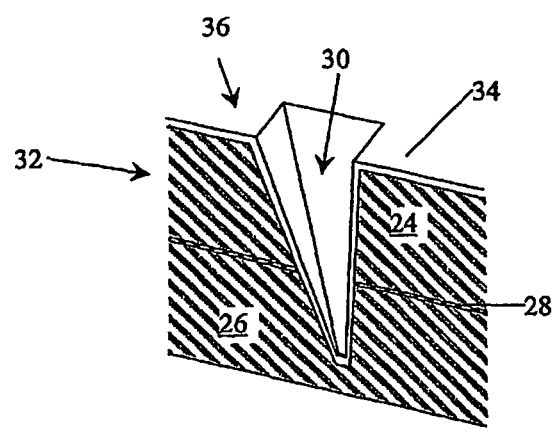
Figure 6

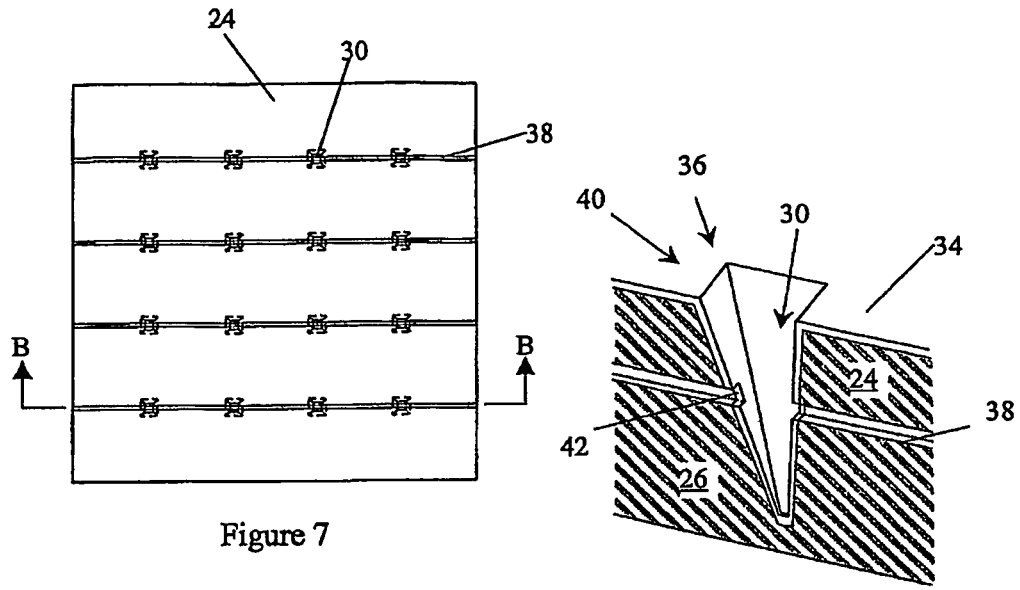
Figure 7
Figure 8B
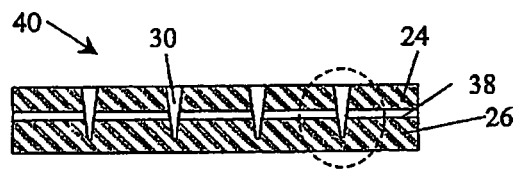
Figure 8A
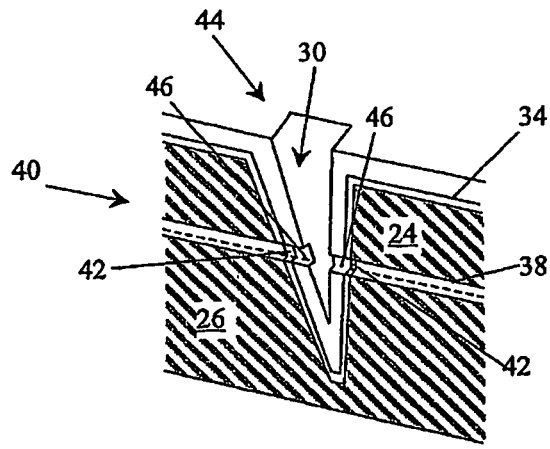
Figure 10

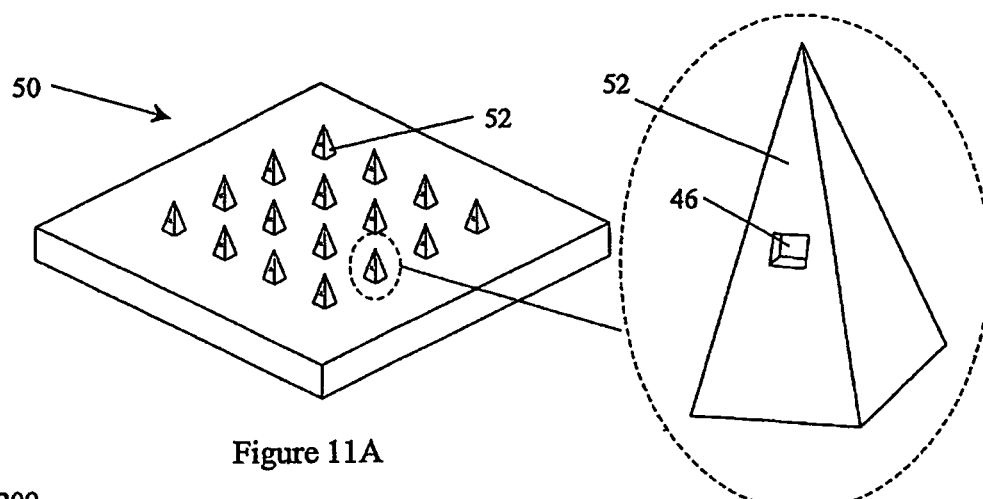
Figure 11A
Figure 11B
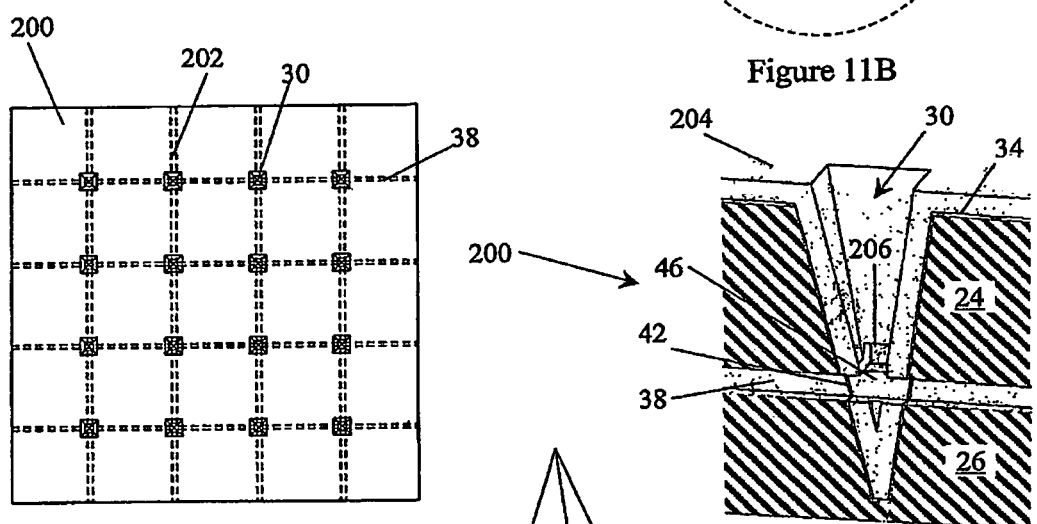
Figure 13A
Figure 13B
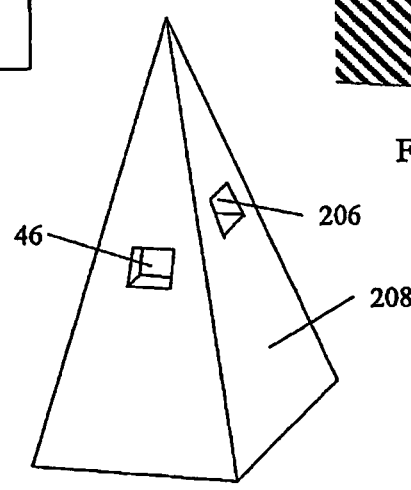
Figure 13C

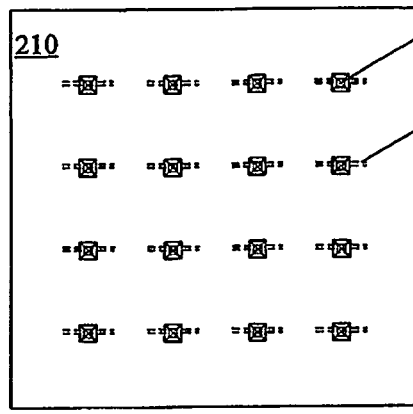
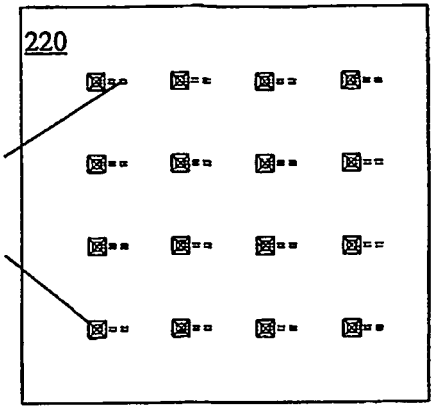
Figure 14A    Figure 15A
Figure 14B
Figure 15B
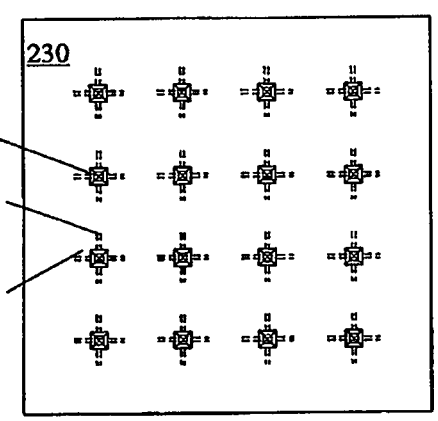
Figure 16A
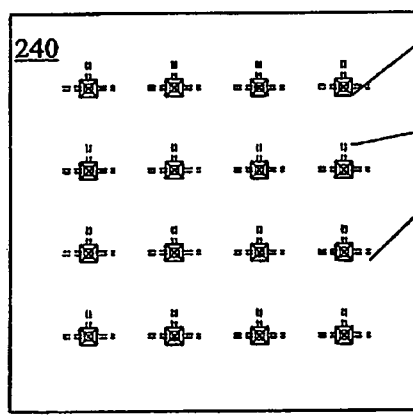
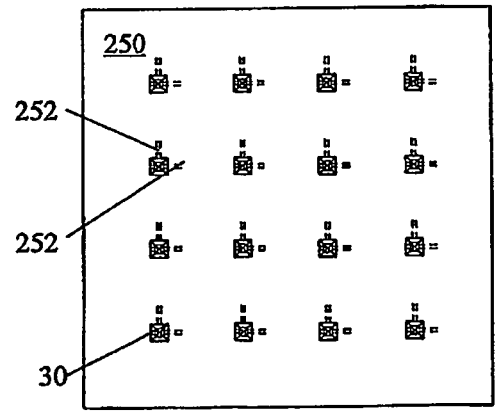
Figure 16B    Figure 16C

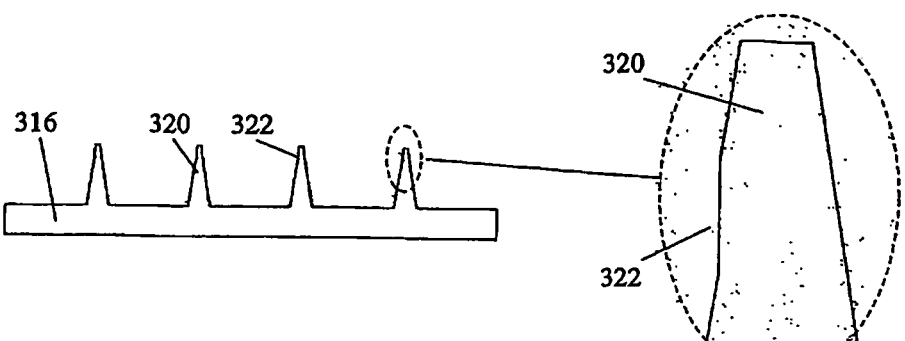
Figure 21A
Figure 21B
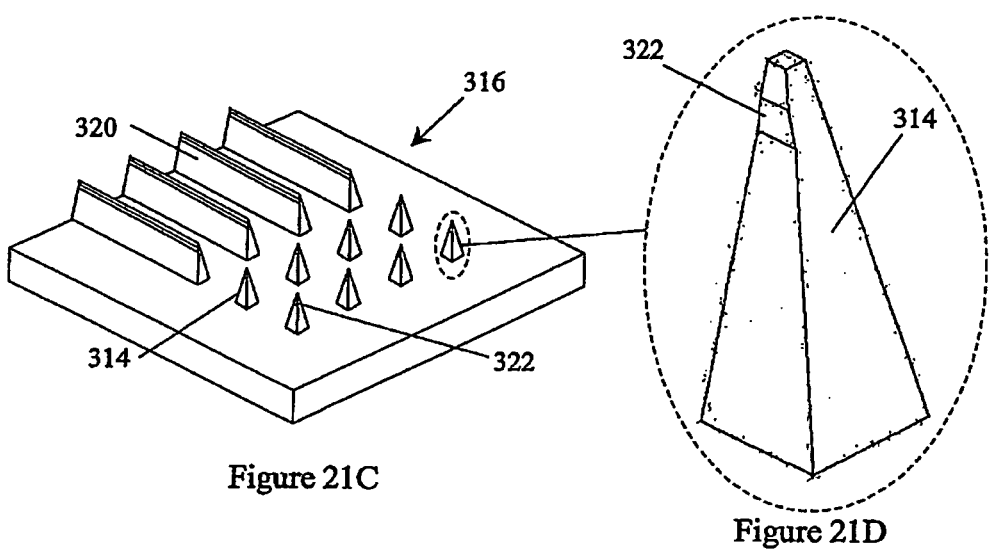
Figure 21C
Figure 21D
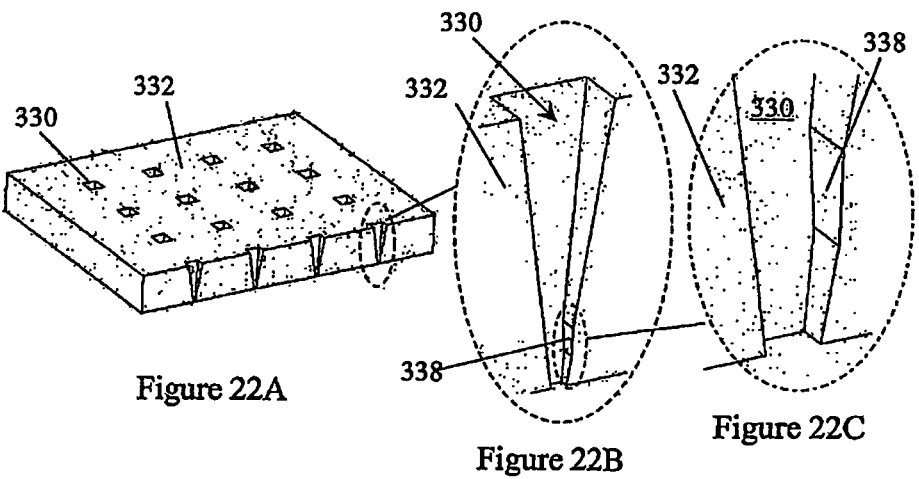
Figure 22A
Figure 22B
Figure 22C

METHODS AND MOULDS FOR USE IN FABRICATING SIDE-PORTED MICRONEEDLES

CROSS-REFERENCE TO RELATED APPLICATIONS

This application claims the benefit of International Patent Application PCT/SG2004/000055 filed 12 Mar. 2004.

FIELD OF THE INVENTION

The present invention relates to side-ported microneedles, that is microneedles with an opening in at least one side surface. In particular it relates to methods and moulds for use in the fabrication of side-ported microneedles, for instance in strays, and to the so-fabricated side-ported microneedles.

BACKGROUND TO THE INVENTION

Microneedles are small needles, typically in the range of from 1 (micron) to 3 mm long and from 10 nm to 1 mm in diameter at their bases, although the ranges can be wider, for instance up to 10 mm long and 2 mm at their bases. Microneedles typically have applications in biomedical devices, for instance for transdermal drug delivery. Existing microneedle fabrication techniques tend to produce microneedles that are too soft (made of polymeric materials), too brittle (made of silicon or glass) and/or too costly, and/or tend to be too unreliable. For transdermal drug delivery applications, where penetration of the outer skin (stratum corneum) is necessary, there are minimum requirements for the strength and ductility of a microneedle. Prices should be low, as microneedles are usually single-use products.

European Patent Application Publication No. EP-A1-1,088,642, published on 4 Apr. 2001 in the name of Becton Dickinson & Co. describes a method of fabricating an array of solid microneedles by moulding. A silicon master mould member with a recessed surface is placed into a mould cavity. A plastic material is pumped into the mould cavity. Microneedles are formed in the recesses in the master mould member.

European Patent Application Publication No. EP-A1-1,287,847, published on 5 Mar. 2003 in the name of Lifescan, Inc. describes a method of fabricating hollow microneedles by plastic injection moulding. The mould is made of two parts. The top part has a conical recess within its moulding surface. One of the top and bottom parts has a protrusion extending to the moulding surface of the other part for forming the needle lumen. The needle lumen forming part meets the conical surface of the top part, such that the out port of the needle lumen in the final needle extends from the tip of the needle and part of the way down only one side, in an eccentric manner.

U.S. Pat. No. 6,334,856, issued on 1 Jan. 2002 to Allen at al. describes various ways of making arrays of hollow microneedles. In one example mocks are formed on the tips of solid microneedles of a silicon microneedle array, a layer of silicon dioxide or metal is coated onto the microneedle array, and the silicon is etched away to leave a hollow microneedle array of metal or silicon dioxide. In another example a layer of epoxy is cast onto an array of solid silicon microneedles. The level of the epoxy is reduced to below the tips of the microneedles. The silicon array is removed, leaving an epoxy microneedle mould. A Ti—Cu—Ti seed layer is splutter-deposited onto the epoxy microneedle mould and Ni—Fe electroplated onto the seed layer. The epoxy layer is then removed, leaving an array of hollow metal microneedles.

U.S. Pat. No. 6,379,324, issued on 30 Apr. 2002 to Gartstein et al. describes various ways of making arrays of hollow microneedles. One way involves self-moulding a polymer film over micro-pillars through heating. A second approach is to place a polymer film over micro-pillars, heat the film and press it down over the micro-pillars using a recessed plate. A third way is to heat a plastic film in the lower part of a mould and to bring the upper part of the mould down onto the lower part. The upper part of the mould has micro-recesses, with micro-pillars protruding from their centres. As the upper part of the mould comes down, the lower parts of the micro-pillars displace the plastic of the plastic film up into the micro-recesses.

Most prior art needles have openings at the tips of the needles, which means they must be of a minimum width there, so limiting their sharpness. Further, as the injected fluid passes out through the axial direction of the needle it faces larger tissue back pressure, requiring a greater force to inject the fluid successfully.

SUMMARY OF THE INVENTION

According to one aspect of the invention, there is provided a method of manufacturing a microneedle mould for use in fabricating microneedles, comprising: providing a microneedle mould base with recesses therein, the recesses corresponding to the microneedles to be fabricated and extending from a first surface of the microneedle mould base; and forming side-port forming holes in the microneedle mould base, the side-port forming holes extending in side surfaces of the recesses within the microneedle mould base at side-port forming positions of the recesses.

The side-port forming holes are preferably formed by forming channels within the microneedle mould base. Alternatively, the side surfaces of the recesses are provided with discontinuities at the side-port forming positions of the recesses and a seed layer is deposited into the recesses after providing the side-port forming discontinuities, with the seed layer failing to deposit substantially on the side-port forming discontinuities.

According to a second aspect of the invention, there is provided a method of manufacturing a master mould for use in making microneedles, comprising providing a master mould having a master mould base surface with a plurality of master mould needles protruding therefrom, the plurality of the master mould needles comprising at least one first side surface with a side-port forming portion thereon extending in a plane substantially orthogonal to the master mould base surface.

According to a third aspect of the invention, there is provided a master mould for use in making microneedles fabricated using the method of manufacturing a master mould of the second aspect.

According to a fourth aspect of the invention, there is provided a master mould for use in making microneedles, comprising: a master mould base surface with a plurality of master mould needles protruding therefrom; wherein a plurality of the master mould needles comprise at least one first side surface with a side-port forming portion; and the side-port forming portions extend on the first side surfaces of the master mould needles in planes that extends substantially orthogonal to the master mould base surface.

According to a fifth aspect of the invention, there is provided a method of manufacturing a microneedle mould for use in fabricating microneedles, comprising moulding a microneedle mould base on a master mould of the third or fourth aspects.

According to a sixth aspect of the invention, there is provided a microneedle mould manufactured using the method of the first or fifth aspects.

According to a seventh aspect of the invention, there is provided a microneedle mould comprising a microneedle mould base with a plurality of recesses extending from a first surface thereof and a plurality of side-port forming holes in the microneedle mould base, the side-port forming holes extending in side surfaces of the recesses within the microneedle mould base at side-port forming positions of the recesses.

According to an eighth aspect of the invention, there is provided a method of fabricating microneedles, using the microneedle mould of the sixth or seventh aspects.

According to a ninth aspect of the invention, there is provided one or more microneedles fabricated using the method of the eighth aspect or using the method or mould of any one or more of the first to seventh aspects.

INTRODUCTION TO THE DRAWINGS

The invention is now further, described by way of non-limitative examples with reference to the accompanying drawings, in which:—

FIGS. 5A to 5C are various views of a microneedle mould base created by the process illustrated in FIG. 4;

FIG. 6 is a perspective view of a portion of the microneedle mould base, with a seed layer coating;

FIG. 7 is a plan view of a second side of a portion of the microneedle mould base after side-port forming channels have been formed therein;

FIGS. 8A and 8B are various views of the reconstructed microneedle mould base, after side-port forming channels have been formed therein;

FIG. 10 is a perspective cross-sectional view of a portion of the microneedle mould plated with a microneedle layer;

FIGS. 11A and 11B are views of a microneedle array and microneedles of a first main embodiment;

FIGS. 13A to 13C are various views relating to the production of a microneedle mould and to forming microneedles, with an alternative side-port forming channel arrangement;

FIGS. 14A and 14B are views of a further alternative microneedle mould with another side-port forming channel arrangement;

FIGS. 15A and 15B are views of another alternative microneedle mould with another side-port forming channel arrangement;

FIGS. 16A to 16C are views of yet further alternative microneedle moulds with other side-port forming channel arrangements;

FIGS. 21A to 21D are various views of a plate being cut into a master mould of a different form, with a discontinuity for a second main embodiment;

FIG. 22A to 22C are various views of a microneedle mould base according to a the second main embodiment;

DETAILED DESCRIPTION

Figure 1:
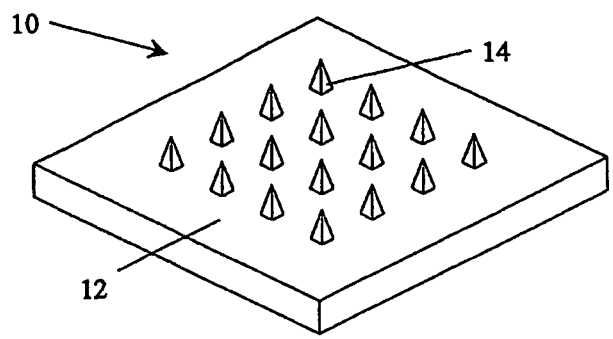
FIG. 1 is a perspective view of a master mould 10 used in the preparation of a microneedle mould.

This description relates to fabricating hollow microneedles with side ports on the lateral surface(s) (side-walls) to enhance delivery efficiency. The methods described can be used to make metallic needles with sufficient strength and ductility. The fabrication cost is low. The side-ported microneedles require no opening at the tip, allowing smaller and sharper tips for skin penetration. Further, liquid delivery through the side port is easier than through the opening at the needle tip, where back-pressure from tissue is higher.

In the drawings, like numerals on different Figures are used to indicate like elements throughout.

A method of fabricating microneedles typically involves three main steps:
(i) making a master mould;
(ii) making a secondary, microneedle mould; and
(iii) forming the microneedles.

The embodiments of the present invention as described herein are particularly concerned with step (ii) making a secondary, microneedle mould and step (iii) forming the microneedles. An example of step (i) making a master mould is described later.

Making a Microneedle Mould—[Step (ii)]

FIGS. 1 to 18 relate to the manufacture of side-ported microneedles and associated processes according to a first main embodiment and variations thereon. In non-limitative summary, a microneedle mould base is made with a number of microneedle mould recesses in it. One surface of the microneedle mould base is coated with a seed layer. The microneedle mould base contains two microneedle mould sheets, which are separated to gain access to an internal surface of one of the microneedle mould sheets. Side-port forming channels are formed on one of the internal surfaces, intersecting with the recesses within the relevant microneedle mould sheet. The two microneedle mould sheets are placed back together and joined together as a unitary microneedle mould. The microneedles are formed in the recesses by depositing a microneedle layer therein and on the surface with the seed layer. The microneedle layer fails to deposit at side-port forming holes, which are where the side-port forming channels intersect or intercept the recesses, which result in side-ports in the moulded microneedles.

FIG. 1 is a perspective view of a master mould 10 used in the preparation of a secondary, microneedle mould. The master mould 10 has a base 12 (which is generally parallelepiped in this embodiment but may be otherwise) from which extends an array of a plurality of master mould needles 14 from one face. The master mould 10 may usefully be made by precision wire cutting, as is described later, or other precision machining, for example CNT machining, or by other methods.

For simplicity only a single master mould needle array is shown in the Figures (except FIG. 2), although fabrication would normally involve an array of many such arrays formed on the master mould and microneedle mould and on the product on which the microneedles are formed.

Figure 2:
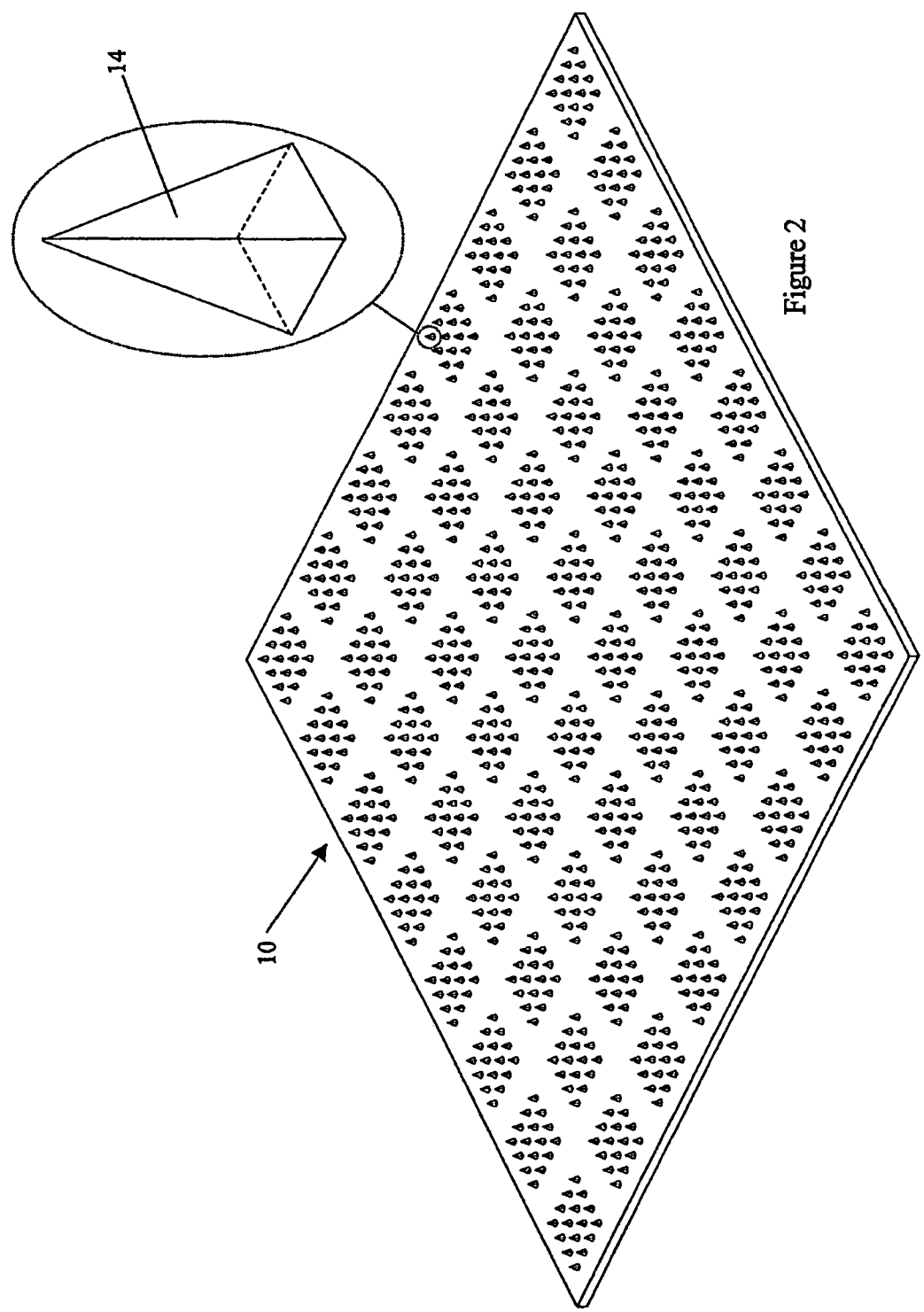
FIG. 2 is an isometric view of a master mould with 64 (8×8) mould needle arrays.

FIG. 2 is a view, for illustration purposes, of an array of eight by eight master mould arrays 10, with an enlarged view of a single master mould needle 14. Of course there may be other sizes and shapes of arrays of needles 14 and master moulds 10.

Figure 3:
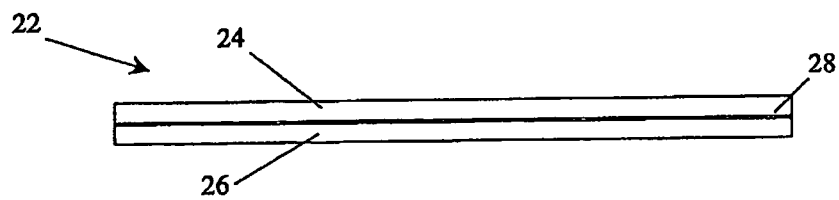
FIG. 3 is a side elevation of an embossing plate, before it is embossed to make a microneedle mould.

FIG. 3 is a side elevation of a blank secondary, microneedle mould plate 22, before it is embossed to make a secondary, microneedle mould. The microneedle mould plate 22 is formed of two overlaid mould base sheets, in this embodiment first and second embossing sheets 24, 26, with a separation layer 28 between them. For the purposes of the Figures, the thickness of the separation layer 28 is exaggerated.

The first and second embossing sheets 24, 26 are, for example, made from a thermoplastic polymeric material such as polycarbonate, polyimide, PMMA, etc. Before placing the two embossing sheets 24, 26 together, to form the microneedle mould plate 22, the separation layer 28 is provided. The two embossing sheets 24, 26 have alignment marks on them (not shown), which may be present before the embossing sheets 24, 26 are put together or may be added after the embossing sheets 24, 26 are put together. The first embossing sheet 24 may typically be anything from 50 to 250 μm (microns) thick and the second embossing sheet 26, anything from 100 to 1500 μm (microns) thick. Whilst the two embossing sheets 24, 26 are shown here to be of roughly the same thickness, they may clearly be of different thicknesses.

The separation layer 28 may be a film applied to the second, bottom surface of the first, upper embossing sheet 24 or the first, top surface of the second, lower embossing sheet 26 or applied to both such surfaces. The purpose of the separation layer 28 is to avoid the bonding together of the two embossing sheets 24, 26, in a later hot embossing step. The separation layer 28 could, for example, be a deposition layer of a metal such as Al, Ti, Cr, etc., a polymer film such as PTFE or a thin layer of a silicone injection mould release agent. The separation layer 28 may typically be anything from 1 to 100 μm (microns) thick.

Figure 4:
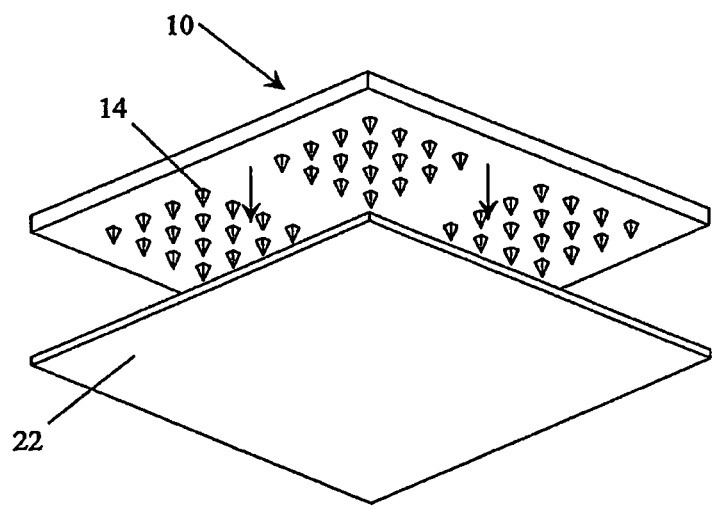
FIG. 4 is an illustrative view of an embossing process for making a microneedle mould base.

FIG. 4 is a view of an embossing process for making a secondary, microneedle mould base. The master mould 10 is fixed horizontally on the top surface of a hot press (not shown) with the master mould needles 14 facing downwards. The microneedle mould plate 22 is placed on a lower plate of hot press (not shown), below the master mould 10. The first, upper embossing sheet 24 is not as thick as the height of the master mould needles 14. The overall thickness of the microneedle mould plate 22 is greater than the height of the master mould needles 14 to prevent the full penetration of the master mould needles 14 through the microneedle mould plate 22.

The master mould 10 is heated to a first temperature, a little over the softening temperature of the microneedle mould plate 22 (for polycarbonate, it is above 150° C., in the range between 150 and 200° C.). At the first temperature, the master mould 10 is pressed down into the microneedle mould plate 22, with the lower plate of the hot press at the same temperature as the master mould 10.

The temperature is allowed to drop to a second value, lower than the softening temperature of the microneedle mould plate 22. At this second temperature value, the microneedle mould plate 22 hardens. The embossed microneedle mould plate 22 is released from the master mould 10, with square pyramid recesses 30 'printed' into it (FIG. 5A). The embossed microneedle mould plate 22 forms an unfinished, microneedle mould base 32. The master mould 10 is reusable for making further microneedle moulds.

FIGS. 5A to 5C are various views of the microneedle mould base 32. FIG. 5A is a top plan view of the microneedle mould base 32. FIG. 5B is a cross-section through the microneedle mould base 32, along line A-A of FIG. 5A. FIG. 5C is an enlarged perspective view of a portion of FIG. 5B, showing a recess 30.

FIG. 6 is a similar view to that of FIG. 5C, but with a seed layer 34 on the microneedle mould base 32. A metallization process is used to add the electrically conductive seed layer 34 to the first, upper surface 36 of the microneedle mould base 32 and to the walls of the recesses 30 (but not to the second, under surface of the microneedle mould base 32). The seed layer 34 can be applied by any of PVD, CVD, thermo-evaporation, electroless plating of Ni or another metal/alloy, through silver mirror reaction for a thin silver layer or some other method. The conductive layer can be metal/alloy or another material such as carbon, diamond like carbon, amorphous carbon, diamond, metal silicide, conductive carbide, etc. The seed layer 34 covers the whole of the top surface 36 as well as lining the recesses 30. The seed layer 34 has a substantially constant thickness, and is typically within the range of between 10 nm and a few microns (or more).

Following metallization, the two embossed embossing sheets 24, 26 are released from each other, which is relatively easy given the presence of the separation layer 28. Side-port forming channels 38 are formed in and across the second, lower surface of the first embossing sheet 24, in this embodiment in the form of grooves within the surface. The sideport forming channels 38 intercept and are centred on the openings of the recesses 30 in the second, lower surface of the first embossing sheet 24 (the recesses 30 are actually throughholes through the first embossing sheet 24). FIG. 7 is a plan view of the second, under side of the first embossing sheet 24 after the side-port forming channels 38 have been formed. The dotted lines in FIG. 7 are the openings of the recesses 34 in the first upper surface 36 of the first embossing sheet 24.

The side-port forming channels 38 may be formed by way of laser ablation, precision machining, lithography or some other means. With the present embodiment, laser ablation with a 355 nm wavelength YAG laser is used for a polycarbonate thin plate 24. The side-port forming channels 38 may have a rectangular, square, triangular, circular, elliptical or other cross-section, normally a regular cross-section, for instance a rectangular cross-section with dimensions around 50 μm (microns) in width by 60 μm (microns) in height. The dimensions of the side-port forming channels 38 vary depending on the needle design.

The separation layer 28 at the interface between the two embossing sheets 24, 26 is removed from either or both the opposing surfaces of the embossing sheets 24, 26 and the two embossing sheets 24, 26 are realigned using the alignment marks mentioned earlier and put together again. The two embossing sheets 24, 26 are joined (bonded) together by a hot press at a temperature and under a pressure which are lower than the hot embossing temperature and pressure, used when embossing the recesses 30 into the microneedle mould plate 22. This reduction in the temperature and pressure is to prevent distortion to the formed structures (recesses 30 and sideport forming channels 38) in the reconstructed microneedle mould base 32, which is now the secondary, microneedle mould 40, which is now a unitary body.

FIGS. 8A and 8B are various views of the reconstructed microneedle mould base, the microneedle mould 40. FIG. 8A is a cross-section through the microneedle mould 40, along a line corresponding to line B-B of FIG. 7. FIG. 8B is an enlarged perspective view of a portion of FIG. 8A, showing a recess 30, intercepted by a side-port forming channel 38.

Figure 9:
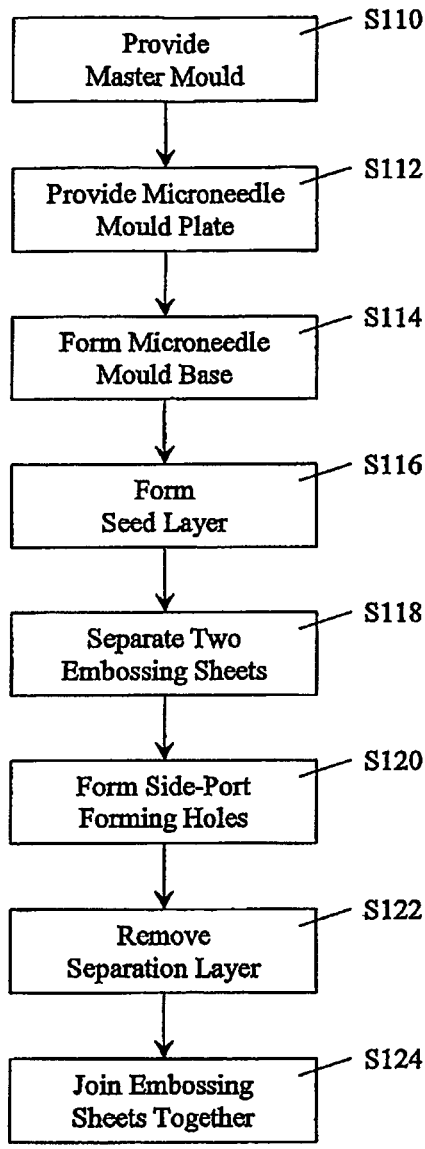
FIG. 9 is a flowchart relating the steps involved in making a microneedle mould according to a first main embodiment.

A flowchart describing the steps involved in making the microneedle mould according to this embodiment is shown in FIG. 9. At step S110 a master mould 10 is provided. At step S112 a microneedle mould plate 22 is provided. At step S114 a microneedle mould base 32 is formed from the microneedle mould plate 22, using the master mould 10. At step S116 the seed layer 34 is formed on the microneedle mould base 32. The two embossing sheets 24, 26 are separated at step S118. The side-port forming channels 38 are formed in the first embossing sheet 24 at step S120. The separation layer 28 is removed at step S122. At step S124, the two embossing sheets 24, 26 are put directly back together and joined together, with the microneedle mould base 32 reconstructed to provide the microneedle mould 40.

Forming the Microneedles—[Step (iii)]

A microneedle mould 40, for instance a microneedle Mould 40 as shown in FIG. 8 and produced as described in the above section is used to form microneedle arrays. The microneedle mould 40 is generally a thin parallelepiped, with recesses 30 in one side. The side surfaces of the recesses and one side of the mould in which the recesses are formed are covered with a seed layer 34. Moreover, there are side-port forming holes 42 in the sides of the recesses 30, including through the seed layer 34 in the recesses. In this embodiment the side-port forming holes 42 are formed by side-port forming channels 38 passing through the microneedle mould 40 from one edge to the other.

Although one way of making a microneedle mould is described above, other ways can be used, for instance by making a unitary microneedle mould base (for instance by injection moulding). Side-port forming discontinuities, such as smaller recesses or side-port forming holes are added within the sides of the main recesses. For example, the side-port forming holes can be added by cutting the microneedle mould base in two, making the side-port forming channels as before, then reuniting the two parts, or by cutting the side-port forming channels through the microneedle mould base from one side to the other without cutting the microneedle mould base in two.

A microneedle layer 44 is provided by electroforming Ni or Ni/Fe alloy or another metal/alloy onto the top surface of the microneedle mould 40. The microneedle layer 44 is formed on top of the thin metal seed layer 34 on the microneedle mould 40 and in the recesses 30, as shown in FIG. 10, showing a recess 30, intercepted by a side-port forming channel 38. FIG. 10 is a perspective cross-sectional view of a portion of the microneedle mould 40, plated with the microneedle layer 44, and corresponds to the views of FIGS. 6 and 8B. The thickness of the plated metal/alloy preferably ranges from 20-100 μm (microns) (although wider ranges are also possible). Other techniques can be used instead of electroforming, for instance electroless plating or vapour deposition, particularly for depositing non-metal layers, such as carbon, although these may be expensive.

The side-port forming channels 38 passing through the recesses 30 create anomalies in the microneedle layer 44 within the recesses 30. In particular, no microneedle layer metal can be deposited over the holes 42 where the side-port forming channels 38 pass through the recesses 30, as there is no seed layer 34 for the metal to grow on. Thus the side-port forming holes 42, where the side-port forming channels 38 pass through the recesses 30 continue as side-ports or holes 46 through the microneedle layer 44 as well.

The plated metal/alloy structure, microneedle layer 44 is released from the microneedle mould 40. Examples of methods of doing this include: a) mechanically peeling the needle layer off, or b) chemically dissolving the mould. Where the microneedle layer 44 is peeled off the plated structure may first be heated up, for instance to a certain temperature. Where this method is to be used, the seed layer that is used is selected to be one with low adhesion to the electroformed needle layer and/or to the mould.

The released structure is the desired microneedle array product 50, as shown in FIG. 11A, with an array of the desired microneedles 52. For simplicity only a single microneedle array is shown in FIG. 11A, although fabrication would normally involve an array of many such arrays being formed (for instance 64 (8×8) arrays, using the master mould of FIG. 2). FIG. 11B is an enlarged view of one of the pyramidal microneedles 52. The holes 46 in the microneedle layer 44 in FIG. 10 are part of the microneedles 52 of the microneedle array product 50, extending through from one side-wall to another. These holes 46 are side-ports, in fluid connexion with the needle lumen extending upwards from the base of the microneedle 52.

The released microneedle mould 40 can be reused or disposed of after the release, where the release method does not damage the mould.

Figure 12:
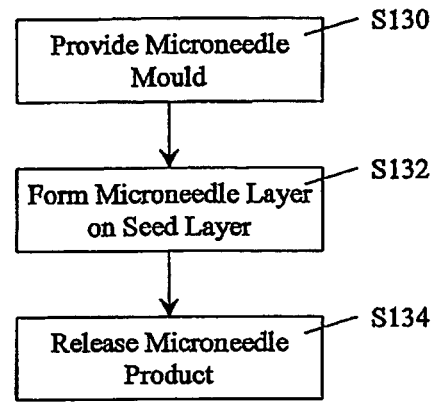
FIG. 12 is a flowchart relating the steps involved in forming the microneedles according to another embodiment.

A flowchart describing the steps involved in making the microneedles according to this embodiment is shown in FIG. 12. At step S130 a microneedle mould 40 is provided. At step S132 a microneedle layer 44 is electroformed onto the seed layer 34 on top of the microneedle mould 40 and in the recesses 30. The microneedle array product 50 is released from the microneedle mould at step S134.

Alternative Geometries and Other Variations of the First Embodiment

The microneedle mould plate 22, used to make the microneedle mould 40, is shown in the above embodiment (with reference to FIGS. 1 to 5) as being thicker than the height of the master mould needles 14. Alternatively, the thickness of the microneedle mould plate 22 and the height of the master mould needles 14 may be the same. The height of the master mould needles 14 may even be greater than the thickness of the microneedle mould plate 22. In the hot-pressing process, the extra height of the master mould needles 14 would then be accommodated into recesses of the lower plate of the hot press or into recesses into an extra plate on top of the lower plate of the hot press. In this manner, the recesses 30 (as shown in FIGS. 5 to 10) in the microneedle mould 40 become through-holes. This can improve the throwing power in the later electroforming step.

In the above-described embodiment, the side-port forming channels 38 are in the second, bottom surface of the first, top embossing sheet 24. In an alternative embodiment, the side-port forming channels 38 are, instead, in the first, top surface of the second, bottom embossing sheet 26. In a further embodiment, the side-port forming channels are in both surfaces. For instance, if they are aligned which each other in the opposing surfaces, it would result in larger holes 46 in the microneedle array product 50. Alternatively the side-port forming channels in the second, bottom surface of the first, top embossing sheet 24 may be at an angle to those in first, top surface of the second, bottom embossing sheet 26.

FIG. 13A is a top plan view of a second mould 200 with a second set of side-port forming channels 202 normal to the first set of side-port forming channels 38 in the opposing surface. FIG. 13B is a perspective cross-sectional view of a portion of the microneedle mould 200 of FIG. 13A, plated with a microneedle layer 204, and corresponds to the views of FIGS. 6, 8B and 10. In addition to the first holes 46, there are also two second holes 206 in the microneedle layer 204 in each recess 30, again due to the absence of seed layer 34 at second side-port forming holes where the second side-port forming channel 202 comes in. A resulting pyramidal microneedle 208 is shown in FIG. 13C, with one hole 46, 206 in each of the four sides. The holes 46, 206 in opposing sides are at the same level, while the holes 46, 206 in adjacent sides are at different levels.

If two sets of side-port forming channels were formed normal to each other in the same surface of one of the two embossing sheets, that is in the second, bottom surface of the first, top embossing sheet 24 or in the first, top surface of the second, bottom embossing sheet 26, the result would be similar to that shown in FIGS. 13A to 13C, but with the side-ports (holes) all at the same level (although possibly of different sizes if the side-port forming channels were of different sizes). However, where there is more than one side-port forming channel passing through a recess, it is preferred to have the side-port forming channels on opposing surfaces of the embossing sheets (that is one in the second, bottom surface of the first, top embossing sheet 24 and a second in the first, top surface of the second, bottom embossing sheet 26). Otherwise four openings at the same level might reduce a microneedle's cross sectional area and its strength too much.

In the above embodiments, the side-port forming channels extend all the way across the relevant embossing sheets, from one side to the other. However, they do not need to extend all the way across or even to be continuous. Instead there may be short separate side-port forming channels in a line, each side-port forming channel crossing into or over only a single recess (or possibly over only two or more but without extending to all recesses in a line). Such an arrangement is shown in FIGS. 14A and 14B. FIG. 14A is a top plan view of an alternative second mould 210 with recesses 30 as before, but with shorter side-port forming channels 212, the side-port forming channels 212 extending only in one direction, through two opposing sides in each recess. FIG. 14B is a cross section through FIG. 14A. The resulting needles appear generally no different from those of FIG. 11B.

Nor do the side-port forming channels necessarily need to extend through both sides of a recess, but can extend instead into only one side of a recess, as in FIG. 15A. FIG. 15A is a top plan view of an alternative second mould 220 with recesses 30 as before, but with shorter side-port forming channels 222, the side-port forming channels extending only in one direction, and extending into only one side of each recess. FIG. 15B is a cross section through FIG. 15A. The resulting needles differ from those of FIG. 11B, in that they have a side-port (hole) in only one side.

FIGS. 16A to 16C show three further variations. FIG. 16A is a top plan view of an alternative second mould 230 with short side-port forming channels 232 that extend across both sides of the recesses 30 in two, normal directions, for example to provide microneedles such as that shown in FIG. 13C. FIG. 16B is a top plan view of an alternative second mould 240 with short side-port forming channels 242, 244 that extend in two, normal directions. However, the side-port forming channels 242 of only one set of side-port forming channels extend through both sides of the recesses 30. The side-port forming channels 244 of the other set of side-port forming channels extend into only one side of each recess 30. FIG. 16C is a top plan view of another alternative second mould 250 with short side-port forming channels 252 that extend into only one side of each recess in two, normal directions.

The side-port forming channels do not need to be long. They only need to create a significant discontinuity in the sides of the recesses, for instance a hole or even just a recess.

In the above embodiment, the microneedle mould plate has two overlapped embossing sheets separated by a single separation layer. In other embodiments, the microneedle mould plate comprises three or more such embossing sheets, one above the other, and all separated from the adjacent plates by a separation layer. Thus for three embossing sheets, there are two separation layers. With this arrangement, all three or more embossing sheets are separated after embossing and side-port forming channels put in as required. This allows two or more holes to appear in a side face of the resulting microneedle.

The general shape of the microneedles reflects the shape of the master mould needles. In the above embodiments, the master mould needles are square pyramidal and therefore so are the microneedles. The master mould needles may, however, be of other shapes, for instance triangular, hexagonal, octagonal, etc. (regular or otherwise). The microneedle moulds based on such master moulds are made as before, but with the directions, lengths and positions of the side-port forming channels altered as required.

Figure 17A:
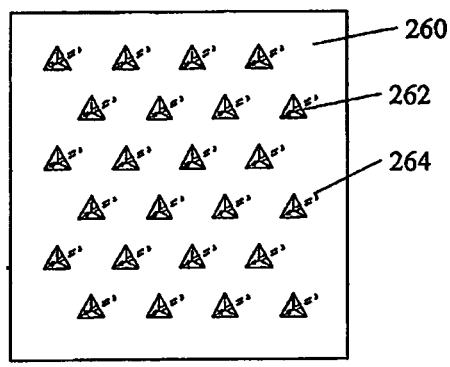
FIGS. 17A and 17B are views relating to the production of triangular side-ported microneedles.
Figure 17B:
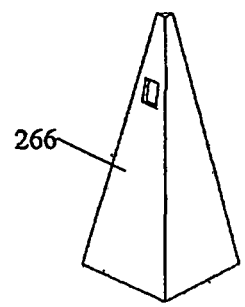

FIG. 17A is a top plan view of an alternative second mould 260 with triangular recesses 262 and short side-port forming channels 264, the side-port forming channels 264 extending only in one direction, and extending into only one side of each recess, at right angles to each recess. FIG. 17B is an isometric view of a microneedle 266 produced using the second mould 260 of FIG. 17A.

The side-port forming channels in the embodiment of FIGS. 17A and 17B are disjointed and extend into only one side of each recess. If the side-port forming channels were continuous, such that they passed all the way across each recess, they would result in a side-port in an edge of each microneedle, opposite the side-port in the front face.

Figure 18A:
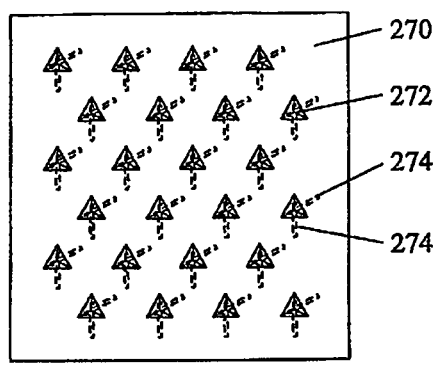
FIGS. 18A to 18D are views of other microneedle moulds for producing other shaped microneedles with other arrangements of side-port forming channels.
Figure 18B:
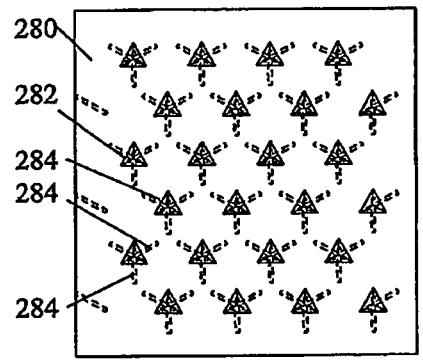
Figure 18C:
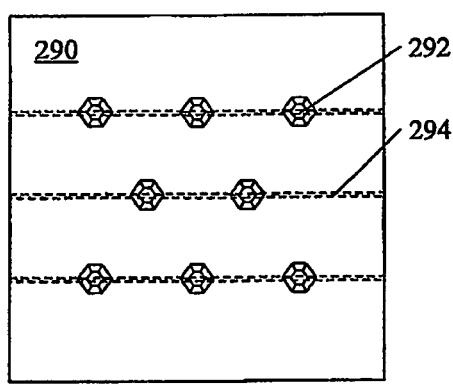
Figure 18D:
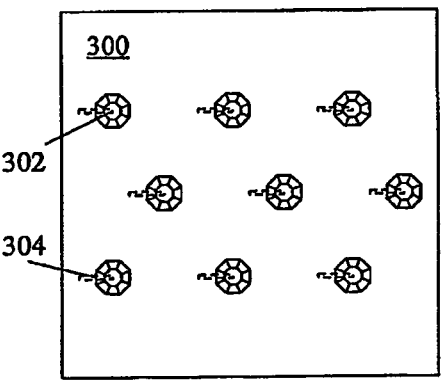

FIGS. 18A to 18D illustrate examples of top plan views of further variations in the recesses and side-port forming channels of the microneedle mould. Of course, there may be Many others. FIG. 18A is a top plan view of an alternative second mould 270 with triangular recesses 272 and short side-port forming channels 274, the side-port forming channels 274 extending in two directions, at 120 degrees to each other, and into two sides of each recess, at right angles to each relevant side. FIG. 18B is a top plan view of an alternative second mould 280 with triangular recesses 282 and short side-port forming channels 284, the side-port forming channels 284 extending in three directions, at 120 degrees to each other, and into the three sides of each recess, at right angles to each relevant side. FIG. 18C is a top plan view of an alternative second mould 290 with hexagonal recesses 292 and long continuous side-port forming channels 294, extending in one direction all the way across each recess, from one side of the microneedle mould 290 to the other. FIG. 18D is a top plan view of an alternative second mould 300 with octagonal recesses 302 and short side-port forming channels 304, the side-port forming channels 304 extending only in one direction, at and into only one side of each recess, at right angles to a side.

The side-port forming channels in all the above embodiments meet the relevant faces of the recesses at ninety degrees and in the centre. Alternatively, the intersection can be at other angles. Moreover the intersection need not be central to any side. For example the side-port forming channels may meet the recesses at a corner and extend all the way along one side or may extend through two adjacent sides etc.

In the order of fabrication of the microneedle mould described above, the side-port forming channels are made after the metallization process. In yet further embodiments, the order of these two operations may be changed, that is the side-port forming channels are formed in the same way as before but before metallization. Metallization does not occur until the microneedle mould base has been reconstructed, that is the embossing sheets put back and joined together. Metallization is conducted using a sputtering technique of a metal/alloy or carbon or another conductive material. Since side-port forming holes or openings are created at the interception locations between the side-port forming channels and the recesses, sputtered atoms cannot be deposited onto these locations. Thus, holes on the deposited seed layer are created. During electroforming, no metal is deposited onto these holes, as before. The holes remain on the electroformed needle wall. After release, microneedle arrays are formed, with side-ports in their walls.

Different variations and alternative approaches mentioned above can be freely combined.

Making a Master Mould—[Step (i)]

Making the master mould 10 as shown in FIG. 1 involves precision machining. A block of material, for example in the form of a parallelepiped tool steel plate (for example AISI A2 or another steel alloy designation) is hardened and all the surfaces are mirror finished. After the finishing, one side of the plate is cut by precision wire cutting (or other precision machining, for example CNT machining), as shown with reference to FIGS. 19A to 19C.

Figure 19A:
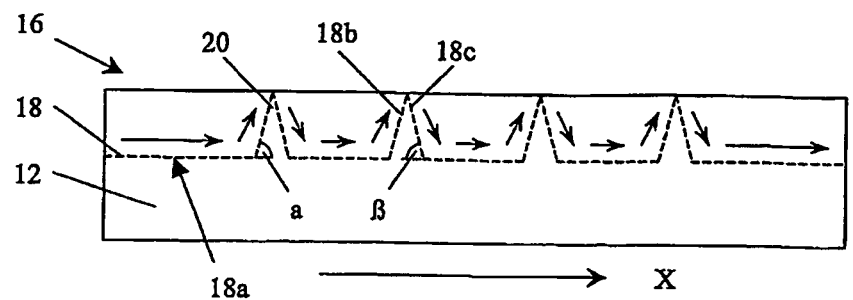
FIGS. 19A to 19C are various views of a plate being cut into the master mould of FIG. 1.
Figure 19B:
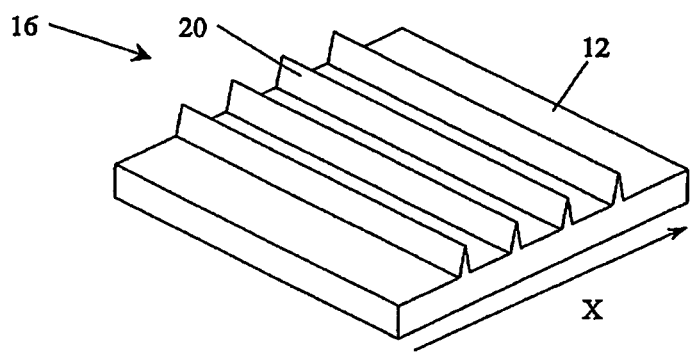
Figure 19C:
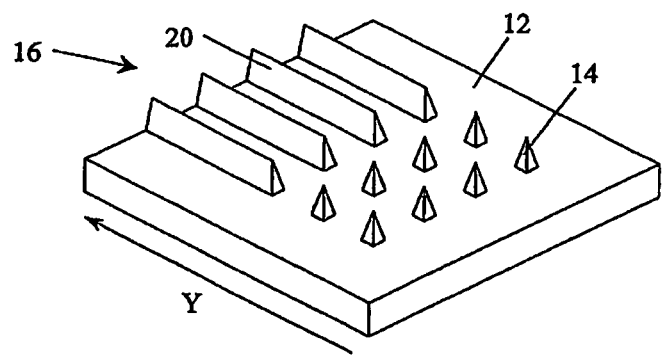

FIG. 19A is a side view of a parallelepiped tool steel plate 16 with mirror finished surfaces, to be out into the master mould of FIG. 1, showing the path a wire takes during one wire cutting pass. FIGS. 19B and 19C are views of the plate of FIG. 19A at different times during the cutting process. FIG. 19B is an isometric view of the same tool steel plate 16 after one pass, in an X direction. FIG. 19C is an isometric view of the same tool steel plate 16 after one pass, in an X direction and half a pass in a Y direction.

The first pass of the wire cutting is conducted in the X direction. FIG. 19A shows the wire cutting line 18. The wire cutting line 18 extends horizontally through the plate 16, at a base level for a base cutting portion 18a, until the position of the first master mould needle line, at which point the wire cutting line 18 extends upwards along a first sloped cutting portion 18b, at a upward cut angle a, being the angle to the surface of the base 12 at which the first sides of the master mould needles extend. At the top surface of the plate 16, the wire cutting line 18 extends downwards again towards the base level. The wire cutting line 18 extends downwards along a second sloped cutting portion 18c, at a downward cut angle β, being the angle to the surface of the base 12 at which the second sides of the master mould needles, opposing the first sides, extend. In this embodiment the upward and downward cut angles a, β are equal, thus first and second sides of the master mould needles are isosceles. In the first pass, this pair of upward and downward cuts, the first and second sloped cutting portions 18b, 18c, creates a ridge 20 between two base cutting portions 18a. The wire cutting line 18 continues horizontally again along the base level for another base cutting portion 18a to the position at which the next needle 14 is to be formed, at which point the wire cutting line 18 extends upwards again and then downwards again, thus cutting another ridge 20. This continues until there are as many ridges 20 as there are to be master mould needles in the X direction.

Ideally at the top of the upward cut, the downward cut begins immediately. However, current wire cutting machines, no matter how accurate they are, always have precision limitations. Thus, when the wire reaches the top of one ridge 20, in practice it must move laterally to some extent (typically 1-20 μm [microns]), before it can go downward. Thus, in practice, the formed ridges 20 and later formed mould needles 14 currently have small flat top surfaces instead of perfect sharp tips. Where the ridges 20 and mould needles 14 appear in the drawings as having perfect sharp tips, instead of small flat tip surfaces, this is for simplicity.

After the first cutting pass, the top part of the plate 16 is removed, leaving parallel ridges on one surface of the steel plate, as appear in FIG. 19B. Then the plate 16 (or the wire cutting tool) is turned 90 degrees around the Z-axis (the direction orthogonally down through the plate 16). A second wire cutting pass in the Y direction is now conducted. This follows the same path as the first pass, as shown in FIG. 19A, except that it is now in a direction at 90 degrees to the direction of the first cut. The upward and downward cuts are at third and fourth side angles. As there is already a first cut, the second wire cutting pass produces individual master mould needles 14, instead of cutting a second row of ridges. FIG. 19C shows the plate 16 half way through the second wire cutting pass. Some master mould needles 14 have been produced and the ridges 20 still extend half way along the plate. At the end of the second wire cutting pass, the plate appears as in FIG. 1. In this embodiment, each master mould needle has the same shape of a square pyramid frustum.

FIGS. 19A to 19C show the fabrication process for a master mould having only one master mould needle array. Several tens or even more master mould needle arrays can be formed by two wire cutting passes, when a larger steel plate is used.

The master mould need not be steel but can be made from another metal/alloy such as an aluminium-alloy, zinc alloy, etc. One or more hard coatings, for example, a diamond carbon coating, a diamond like carbon coating (DLC), an electroless Ni coating, a hard chrome coating, a nitride coating, a carbide coating or a boride coating may be applied onto the master mould surface and master mould needles. This is to increase the hardness of the master mould, to extend the life of the master mould. Additionally or instead there may be added a coating layer, for example a carbon coating, a diamond like carbon coating or some or appropriate coating to facilitate the release of a plate used in the creation of a microneedle mould. Some of the coatings can have both functions: increase hardness and act as a release layer.

Figure 20:
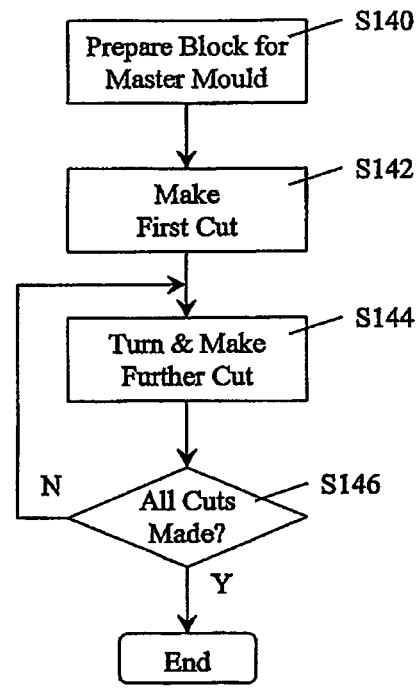
FIG. 20 is a flowchart relating to the manufacture of a master mould.

A flowchart describing the steps involved in making the master mould according to this embodiment is shown in FIG. 20. At step S140 a block of material is prepared. A first cut is made in the block in a first direction at step S142, to form a plurality of ridges. The block is turned and cut again at step S144. A determination is made at step S146 as to whether all the cuts have been made (that is that the cutting has finished, the ridges having been turned into master mould needles). If all the cuts have been made, the process stops. If not all the cuts have been made, the process reverts to step S144.

The sizes and geometries of the final microneedles 52 on the microneedle array product 50 (FIG. 11A) can be adjusted by changing the wire-cutting route 18 in making the master mould 10. With the cutting line 18 shown in FIG. 19A (repeated in the Y direction), the four side surfaces of the master mould needles 14 (and therefore the final microneedles 52) have the same shape, the same inclination angles with respect to the bottom surface, and a square cross section. By changing the uphill and downhill cut angles a, β of the cutting route, the master mould needle shape can be adjusted. Such master moulds of different geometries can be used to form microneedle moulds of different geometries in the same manner as is described above. These microneedle moulds of different geometries can be used to make microneedle array products, again in the same manner as mentioned above.

In the above-described embodiments, the master mould needles and the ultimately produced microneedles have quadrilateral cross-sections arising from a square base. By changing the number of wire cutting passes and/or the angle through which the plate 16 is turned between each cut, other shapes are produced, for instance the triangular, hexagonal and octagonal shapes mentioned earlier (for instance, the triangular or hexagonal master mould needles by using 3 cuts at 120 degrees to each other—but with different down positions—and the octagonal master mould needles by using 4 cuts at 45 degrees to each other). This approach can readily be used to make triangular, square, rectangular, rhomboidal, parallelogram, trapezium shapes or some special non-regular pentagonal, regular and some special non-regular hexagonal, regular octagonal or possibly some other shaped master mould needles.

Second Main Embodiment

A second main embodiment for making microneedles with side openings is now described. This method does not use two or more stacked embossing sheets as in the above-described first main embodiment and its variations. Instead the anomalies in the microneedle layer are introduced through the production process in the master mould.

During the production of the master mould, a short part of one side of each master mould needle is made normal to the base surface of the master mould. The variant master mould may, for instance be made by way of a similar process to that employed to make the master mould of FIGS. 1 and 2. Such a process is now described with reference to FIGS. 21A to 21D.

FIG. 21A is a side view of a tool steel plate 316 after a first cut, in a similar manner to the first cut made to produce the part formed master mould of FIG. 19B (although producing a slightly blunter ridge in this embodiment). A first parallel set of ridges 320 has been produced. However, a difference can be seen in FIG. 21B, which is an enlarged view of a portion of FIG. 21A. There is a side-port forming portion in the form of a discontinuity 322 in the upward slope of one side of the ridges 320, where the slope changes from a first, upward direction to a second, substantially vertical direction, before changing back again to the first, upward direction to reach the crest of the ridge 320. This vertical portion or discontinuity 322 in the slope is achieved by carefully controlling the upward movement angle of the wire in the upward cut.

The second cut, in the second direction is carried out normally, without any change in direction during the upward cut. FIG. 21C is an isometric view of the tool steel plate 316, part way through the second cut. FIG. 21D is an enlarged view of one of the master mould needles 314 produced up to this time. In the final master mould, each mould needle 314 has a vertical part 322 on one of its side surfaces.

A microneedle mould is manufactured from a master mould with discontinuities for instance as described above with reference to FIGS. 21A to 21D. A microneedle mould base is made by hot pressing a microneedle mould plate onto the master mould. The hot-pressing operation is carried out in a similar manner to the hot-pressing method described earlier. However, there is a major difference in the make-up of the microneedle mould plate. The microneedle mould plate is not a stack of two embossing layers with a separation layer therebetween. Instead it is just a single embossing sheet of a similar material as either of the two (or more) embossing sheets in the earlier embodiment and of the same thickness as the height of the master mould needles 314.

The result of the hot pressing is a microneedle mould base 332 as shown in FIG. 22A, which has square pyramid frustum through-holes 330 printed into it, from one side through to the other. FIG. 22B is an enlarged perspective view of a portion of FIG. 22A, showing a recess 330. FIG. 22C is an enlarged view of a portion of FIG. 19B, showing a recess discontinuity 338 in one surface of the recess 330, corresponding to the discontinuity 322 in the master mould needle 314. The recess discontinuity is generally normal or orthogonal to the top and bottom surfaces of the microneedle mould base 332.

Figures 23A, 23B:
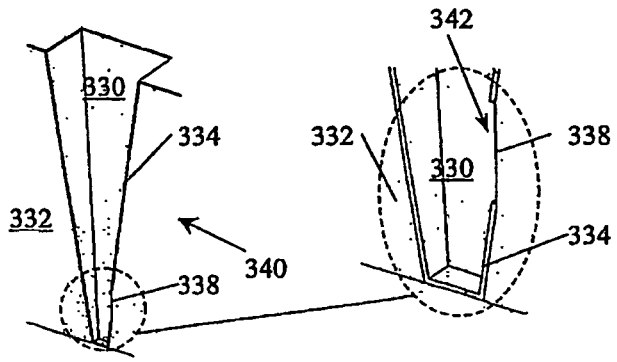
FIGS. 23A and 23B are views of the enlarged portion of the views in FIGS. 22B and 22C, after metallization.

The microneedle mould base 332 is metallized with a conductive seed layer 334, as with the first embodiment. In this embodiment, sputtering is the preferred technique. The sputtered metal atoms pass down into the top of the recess 330 the orientation of FIGS. 22A, 22B and 22C) and fly downwards in an almost straight vertical line to the surfaces of the square pyramid frustum and are deposit at the bottom of the recess 330 and on the major parts of the sidewall that have an inclination angle to the mould upper surface. However, few atoms are deposited on the parts that are normal to the upper mould surface (or parallel to the direction of movement of the atoms into the recess 230. FIG. 23A is an enlarged perspective view of a portion of FIG. 22A, showing a recess 330, after sputtering. FIG. 23B is an enlarged view of a portion of FIG. 23A. The sputtered seed layer 334 extends over the top of the microneedle mould base 332 as well as into the recess 330, on every surface except the recess discontinuity 338. The seed layer did not settle on the vertical wall portion and thus a side-port forming hole or opening 342 is created at that wall part of the seed layer 334. The microneedle mould base 332 and seed layer 334 together form the microneedle mould 340.

Figures 24A, 24B:
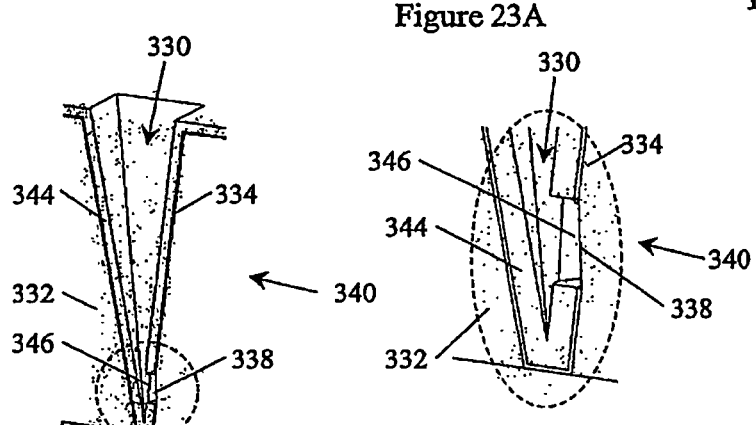
FIGS. 24A and 24B are views of the enlarged portion of the views in FIGS. 22B and 22C, after metallization and electroforming.

An electroforming step takes place onto a microneedle mould 340, for instance a microneedle mould 340 as produced using the process discussed with reference to FIGS. 22A to 23B. The electroforming step takes place as described above with reference to the first embodiment. A microneedle layer 344 is provided by electroforming Ni or Ni/Fe alloy or another metal/alloy onto the top surface of the microneedle mould 340. The microneedle layer 344 is formed on top of the thin metal seed layer 334 on the microneedle mould 40 and in the recesses 330, as shown in FIGS. 24A and 24B. FIG. 24A is an enlarged perspective view of a portion of FIG. 22A, showing a recess 330, after sputtering and after electroforming. FIG. 24B is an enlarged view of a portion of FIG. 24A. The electroformed microneedle layer 344 extends over the top of the microneedle mould base 332 covered by the seed layer 334, as well as into the recess 330 covered by the seed layer 334, on every surface where the seed layer 334 is present. The microneedle layer 344 does not extend over the discontinuity 338 or the seed layer opening 342, as the seed layer did not settle there. There is thus a hole 346 in the side surface of the microneedle layer 344 within the recess 330.

Figures 25A, 25B:
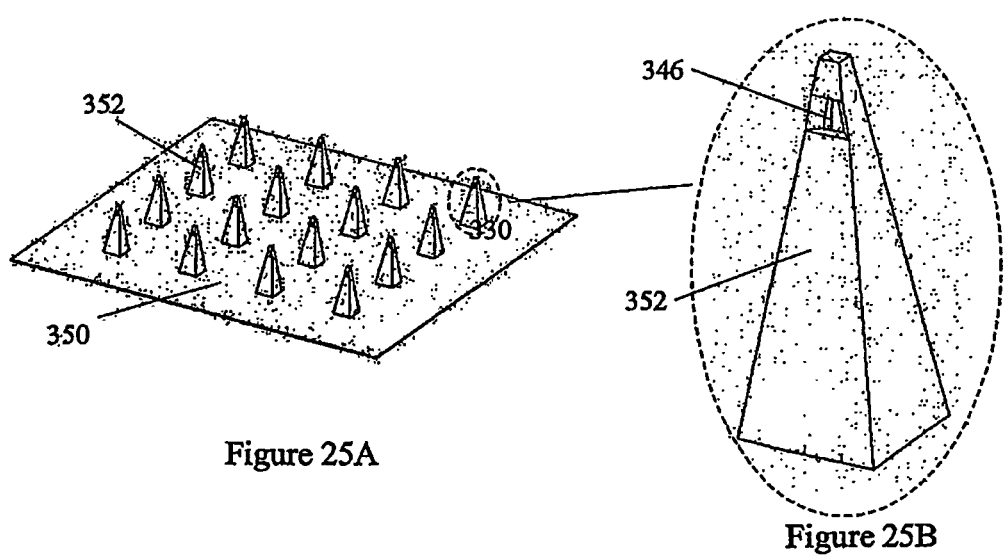
FIGS. 25A and 25B are views of a microneedle army and microneedles of a second main embodiment.

The plated metal/alloy structure, microneedle layer 344 is released from the microneedle mould 340. The released structure is the desired microneedle array product 350, as shown in FIG. 25A, with an array of the desired microneedles 352. FIG. 25B is an enlarged view of one of the pyramidal microneedles 352. The holes 346 in the microneedle layer 344 in the recesses are part of the microneedles 352 of the microneedle array product 350, extending into one side-wall, as side ports, in fluid connexion with the needle lumen extending upwards from the base of the microneedle 352.

The side-ports 346 produced in this manner extend the whole way across the outer surface of one side of the microneedles 352. This is a result of the production method for the master mould as it is described above, although may not necessarily be present from other production methods. The width of the holes 346 through the walls of the microneedles 352 does reduce towards the inner surface of the wall, as more material was electroformed on the seed layers 334 on the sides.

As is apparent, the discontinuity 322 is only on one side of the master mould needle 310 in FIG. 21D, and therefore on only one side of the resultant microneedle 352. However; additional discontinuities can be introduced on the same face, at different levels, and/or on different faces. Moreover, the discontinuity 322 does not need to be produced during just the upward cut, it can be during the downward cut. Nor does the discontinuity 322 need to be produced during the first cut, but can be during the second (or a further) cut.

Moreover, the side-ports produced in this manner are not restricted to being on square-based microneedles, but can be on almost any other shape of microneedles, where a vertical surface can be provided in the microneedle recess within the microneedle mould.

In the above description, the microneedle mould is a secondary mould. There is, however, no absolute requirement that the microneedle mould be produced by way of or from a master mould.

The embodiments of the invention allow the easy production of strong and ductile hollow microneedle arrays or solid needles, such as solid polymer needles, on a large industrial scale. Moulds for fabricating microneedles can be made using cheap polymeric materials so the moulds can be of low cost and disposable. Moreover the exemplary method of making the microneedle mould is cheaper using the wire cutting method to make the master mould. The use of the wire cutting method allows easy variation in the size and shape of the microneedles, whether regular or irregular, tapered or non-tapered, straight or slanted or of various numbers of sides. The sharpness of such microneedles can be further enhanced; holes are not needed at the ends, since the microneedles have side openings, which makes the penetration of the needle through the skin and liquid injection easier. Such microneedle arrays can be used in painless injection devices to replace conventional injection needles/syringe.

Whilst various embodiments are described herein, the invention is not limited thereto. Other variations would be readily apparent to the man skilled in the art which still fall within the scope of the invention, for instance as defined in the appended claims.

The invention claimed is:

1. A method of manufacturing a microneedle mould for use in fabricating microneedles, comprising:
providing a microneedle mould base with recesses therein, the recesses corresponding to the microneedles to be fabricated and extending from a first surface of the microneedle mould base;
forming side-port forming holes in the microneedle mould base, the side-port forming holes extend in side surfaces of the recesses within the microneedle mould base at side-port forming positions of the recesses; and
providing a seed layer on the first surface of the microneedle mould base and in the recesses,
wherein forming the side-port forming holes comprises:
providing the side surfaces of the recesses with discontinuities at the side-port forming positions of the recesses; and
depositing the seed layer after providing the side-port forming discontinuities, with the seed layer failing to deposit substantially on the side-port forming discontinuities.

2. A method according to claim 1, wherein the side-port forming holes extend in the sides of the recesses without extending to the tops or bottoms of the recesses.

3. A method according to claim 1, wherein the side-port forming holes extend in only one side surface of the individual recesses.

4. A method according to claim 3, wherein individual recesses are intercepted by the side-port forming holes at only one point.

5. A method according to claim 1, wherein the side-port forming holes extend in opposing side surfaces of the individual recesses.

6. A method according to claim 1, wherein the side-port forming holes extend in adjacent side surfaces of the individual recesses.

7. A method according to claim 1, wherein providing the side surfaces of the recesses with discontinuities comprises forming portions of the side surfaces of the recesses that are generally orthogonal to the first surface of the mould base.

8. A method according to claim 7, wherein the generally orthogonal portions of the side surfaces of the recesses are formed with the recesses.

9. A method according to claim 1, wherein providing the side surfaces of the recesses with discontinuities comprises forming side-port forming channels in the mould base intercepting the recesses.

10. A method according to claim 9, wherein the side-port forming channels extend from one edge surface of the microneedle mould base to an opposing edge surface of the microneedle mould base, generally parallel to the first surface of the microneedle mould base.

11. A method according to claim 9, wherein the side-port forming channels extend between adjacent recesses.

12. A method according to claim 9, wherein:
the microneedle mould base comprises a plurality of overlaid mould base sheets; and further comprising:
forming the side-port forming holes in the mould base, comprising:
separating the plurality of mould base sheets;
forming side-port forming channels in at least one of the opposing surfaces of at least one of the mould base sheets; and
overlaying the plurality of mould base sheets to reconstruct the microneedle mould base.

13. A method according to claim 12, wherein the side-port forming channels in at least one of the opposing surfaces are formed as grooves in the at least one of the opposing surfaces.

14. A method according to claim 12, wherein the microneedle mould base further comprises a separation layer between the or each two adjacent overlaid mould base sheets.

15. A method according to claim 14, further comprising removing the one or more separation layers prior to overlaying the plurality of mould base sheets to reconstruct the microneedle mould base.

16. A method according to claim 1, wherein the side-port forming holes are formed where side-port forming channels in the mould base intercept the recesses in the mould base.

17. A method according to claim 1, wherein the recesses are through-holes extending from the first surface of the microneedle mould base to an opposing second external surface.

18. A method according to claim 1, wherein providing a microneedle mould base comprises moulding the microneedle mould base on a master mould having a master mould base surface with a plurality of master mould needles protruding therefrom, the master mould needles corresponding to the recesses in the microneedle mould base.

19. A method according to claim 18, wherein the microneedle mould base is moulded on the master mould by hot pressing.

20. A method according to claim 18, further comprising providing the master mould.

21. A method according to claim 20, wherein providing the master mould comprises wire cutting the master mould from a master mould block.

22. A microneedle mould fabricated according to the method of claim 1.

23. A microneedle mould comprising a microneedle mould base with a plurality of recesses extending from a first surface thereof and a plurality of side-port forming holes in the microneedle mould base, the side-port forming holes extending in side surfaces of the recesses within the microneedle mould base at side-port forming positions of the recesses,
wherein the side surfaces of the recesses are provided with discontinuities at the side-port forming positions of the recesses, and
a seed layer is deposited on the first surface of the microneedle mould base and in the recesses, with the seeding layer failing to deposit substantially on the side-port forming discontinuities.

24. A microneedle mould according to claim 23, wherein the side-port forming holes comprise the interception of side-port forming channels in the mould base and recesses in the mould base.

25. A microneedle mould according to claim 23, wherein the discontinuities in the side surfaces of the recesses extend substantially orthogonally to the first surface of the microneedle mould base.

26. A microneedle mould according to claim 23, wherein the discontinuities comprise gaps in the seed layer.

27. A method of fabricating microneedles, comprising:
providing a microneedle mould fabricated according to a method of manufacturing a microneedle mould for use in fabricating microneedles, the method of manufacturing a microneedle mould comprising:
providing a microneedle mould base with recesses therein, the recesses corresponding to the microneedles to be fabricated and extending from a first surface of the microneedle mould base; and
forming side-port forming holes in the microneedle mould base, the side-port forming holes extend in side surfaces of the recesses within the microneedle mould base at side-port forming positions of the recesses;
forming a microneedle layer onto a first surface of the microneedle mould and within the recesses of the microneedle mould, with gaps in the layers on the side-port forming holes; and
removing the microneedle layer from the microneedle mould, the portions of the microneedle layer corresponding to the side-port forming holes comprising microneedle side-ports.

28. A method according to claim 27, wherein the microneedle layer within the recesses is hollow, to form hollow microneedles, the hollow of the microneedles and the microneedle side-ports being in fluid communication.

29. A method according to claim 27, further comprising splitting the microneedle layer into a plurality of microneedle portions, each microneedle portion having one or more microneedles thereon.

30. A method according to claim 27, wherein forming the microneedle layer comprises electroplating, PVD, CVD, thermo-evaporation or electroless plating the microneedle layer onto the first surface of the microneedle mould and into the recesses.

31. A method according to claim 27, wherein removing the microneedle layer from the microneedle mould comprises peeling the microneedle layer off from the microneedle mould.

32. A method according to claim 27, wherein removing the microneedle layer from the microneedle mould comprises dissolving the microneedle mould.

33. One or more microneedles manufactured according to the method of claim 27.

* * * * *

UNITED STATES PATENT AND TRADEMARK OFFICE
CERTIFICATE OF CORRECTION

PATENT NO. : 8,671,544 B2  Page 1 of 1
APPLICATION NO. : 10/592559
DATED : March 18, 2014
INVENTOR(S) : Yuan Xu et al.

It is certified that error appears in the above-identified patent and that said Letters Patent is hereby corrected as shown below:

Title page, item [57] in the abstract, lines 1, 2, 6, 7 and 9: every occurrence of "mold" should be --mould--

In the Specification

Column 1, line 18, "strays" should be --arrays--
Column 1, line 58, "mocks" should be --masks--
Column 4, line 18, "army" should be --array--
Column 4, line 28, "opening" should be --openings--
Column 11, line 34, "out" should be --cut--

Signed and Sealed this
Twenty-second Day of July, 2014

Michelle K. Lee
*Deputy Director of the United States Patent and Trademark Office*

UNITED STATES PATENT AND TRADEMARK OFFICE
CERTIFICATE OF CORRECTION

PATENT NO.       : 8,671,544 B2
APPLICATION NO.  : 10/592559
DATED            : March 18, 2014
INVENTOR(S)      : Xu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2319 days.

Page 1 of 1

Signed and Sealed this
Twenty-ninth Day of September, 2015

Michelle K. Lee
*Director of the United States Patent and Trademark Office*